United States Patent [19]

Fukunaga et al.

[11] Patent Number: 5,482,929
[45] Date of Patent: Jan. 9, 1996

[54] COMPOSITION OF STABILIZED FIBROBLAST GROWTH FACTOR

[75] Inventors: Kazuhiro Fukunaga; Shigeki Hijikata; Kimihiro Ishimura; Yoshiro Ohtani; Kunio Kimura; Masahiro Fujii; Yoshiyuki Hata, all of Tokyo, Japan

[73] Assignee: Kaken Pharmaceutical Co., Ltd., Japan

[21] Appl. No.: 996,392

[22] Filed: Dec. 23, 1992

[30] Foreign Application Priority Data

Dec. 26, 1991 [JP] Japan .................................. 3-357821

[51] Int. Cl.⁶ .............................. C07K 7/00; A61K 38/16
[52] U.S. Cl. .............................. 514/12; 530/399; 530/324
[58] Field of Search .............................. 514/12; 530/399, 530/324

[56] References Cited

U.S. PATENT DOCUMENTS

| | | | |
|---|---|---|---|
| 4,020,160 | 4/1977 | Bernstein et al. | 424/180 |
| 4,247,535 | 1/1981 | Lewis et al. | 424/180 |
| 4,258,034 | 3/1981 | Joseph et al. | 424/180 |
| 4,258,180 | 3/1981 | Lewis et al. | 536/112 |
| 4,378,347 | 3/1983 | Franco | 424/361 |
| 5,135,919 | 8/1992 | Folkman | 514/24 |

FOREIGN PATENT DOCUMENTS

| | | | |
|---|---|---|---|
| 0345660 | 12/1989 | European Pat. Off. | A61K 37/02 |
| 345669 | 12/1989 | European Pat. Off. | A61K 37/02 |
| 406856 | 1/1991 | European Pat. Off. | A61K 37/36 |
| 457223 | 11/1991 | European Pat. Off. | C07K 15/00 |
| 497341 | 8/1992 | European Pat. Off. | A61K 37/02 |
| WO9010456 | 9/1990 | WIPO | A61K 37/02 |

*Primary Examiner*—Jill Warden
*Assistant Examiner*—Carol A. Salata
*Attorney, Agent, or Firm*—Rosenman & Colin

[57] ABSTRACT

A composition of a stabilized fibroblast growth factor (FGF), which contains an aluminum salt of cyclodextrin sulfate to stabilize FGF. FGF can be stabilized by forming a composition of FGF and an aluminum salt of cyclodextrin sulfate, and can be stably prepared into formulations.

8 Claims, 2 Drawing Sheets

COMPOSITION OF STABILIZED FIBROBLAST GROWTH FACTOR

BACKGROUND OF THE INVENTION

1. Field of the Invention

The present invention relates to a composition of a stabilized fibroblast growth factor (hereinafter abbreviated as FGF).

2. Prior Art

In 1974, Gospodarowicz found FGF in bovine pituitary gland to be a protein which highly stimulates the proliferation of fibroblast (Nature, vol. 24, page 123, 1974). FGF genes have been cloned, and it has been made possible to produce them in large quantities by genetic recombination technologies. FGF has been hence energetically studied. As a result, it has been revealed that FGF simulates the proliferation of a variety of cells such as capillary endotherial cells, blood vessel smooth muscle cells, cornea endotherial cells, osteoblast and chondrocyte as well as the proliferation of fibroblast.

Like other polypeptides, however, FGF is easily affected by protease, heat, pH, etc., and it has been therefore considered difficult to prepare any practical FGF formulations.

For stabilizing FGF, a method using water-soluble polysaccharide (JP-A-63-152524 as published in corresponding laid-open patent publication EP 0 267 015) and a method using sulfated glucan (JP-A-2-138223 as published in corresponding laid-open patent publication EP 0 345 660) are disclosed. In the method using sulfated glucan, for example, there is disclosed a formulation containing free cyclodextrin sulfate or a formulation containing cyclodextrin sulfate in the form of a highly water-soluble salt such as sodium salt, potassium salt, ammonium salt or trimethylammonium salt. Since, however, the above methods are not yet satisfactory, the present inventors have made a study to improve the stability of FGF to protease, heat, pH, etc.

SUMMARY OF THE INVENTION

The present inventors have made a diligent study to achieve the above object, and have found that FGF can be stabilized by bringing FGF into contact with an aluminum salt of cyclodextrin sulfate. On the basis of this finding, the present invention has been completed.

According to the present invention, therefore, there is provided a composition of a stabilized FGF, which contains an aluminum salt of cyclodextrin sulfate to stabilize FGF.

DETAILED DESCRIPTION OF THE INVENTION

Figure 1:
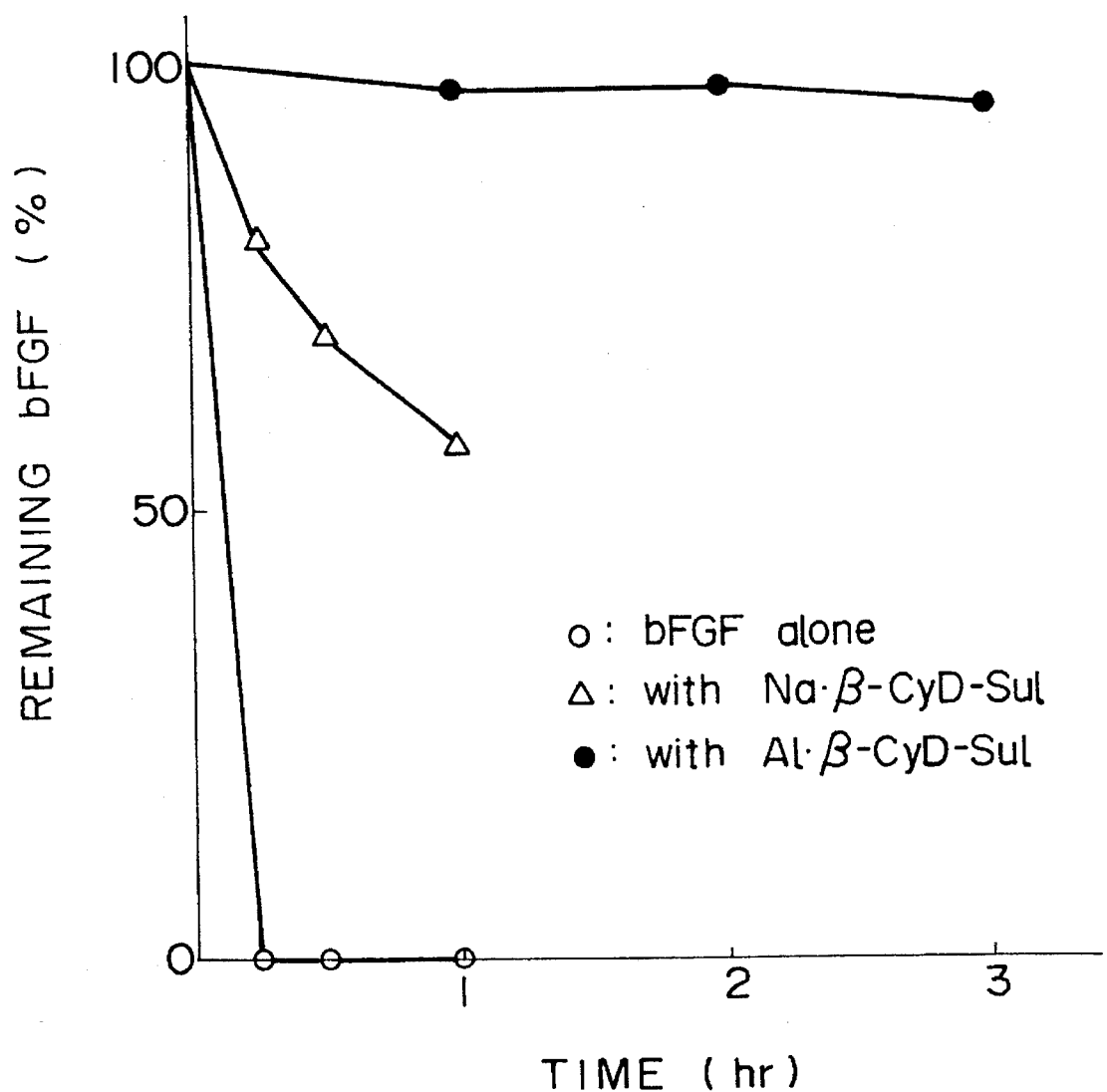
FIGS. 1 and 2 are graphs showing the stability of bFGF with or without a stabilizer.

FGF used in the present invention may be basic FGF (hereinafter abbreviated as bFGF), and it may be also an acidic FGF (hereinafter abbreviated as aFGF). FGF used in the present invention may be that which is isolated from natural sources or produced by recombination DNA technologies.

The cyclodextrin sulfate in the aluminum salt of cyclodextrin sulfate used in the present invention includes sulfuric acid ester derivatives of α-cyclodextrin, β-cyclodextrin, γ-cyclodextrin, hydroxypropyl-α-cyclodextrin, hydroxypropyl-β-cyclodextrin, hydroxypropyl-γ-cyclodextrin, hydroxyethyl-α-cyclodextrin, hydroxyethyl-β-cyclodextrin and hydroxyethyl-γ-cyclodextrin.

The sulfuric acid esters of cyclodextrins can be prepared by a conventional method such as by reacting b-cyclodextrin with $(CH_3)_3NSO_3$ in DMF, with precipitation and filtration procedures as described hereinafter; and as generally known from U.S. Pat. No. 2,923,704.

In the aluminum salt of cyclodextrin sulfate used in the present invention, the number of sulfonyl groups per molecule of the cyclodextrin is at least two, preferably at least four. The amount of aluminum preferably corresponds to the number of the sulfonyl groups. Cyclodextrins whose sulfation degrees are different may be used as a mixture or alone.

The composition of stabilized FGF can be obtained by adding and mixing a solution containing FGF to/with a powdery aluminum salt of cyclodextrin sulfate or adding and mixing FGF to/with a suspension of an aluminum salt of cyclodextrin sulfate. In the composition of stabilized FGF, FGF is adsorbed on the aluminum salt of cyclodextrin sulfate. In the so-obtained composition of stabilized FGF, the mixing ratio of FGF/aluminum salt of cyclodextrin sulfate is 1/2 to 1/500. In the composition of stabilized FGF, provided by the present invention, FGF and the aluminum salt of cyclodextrin sulfate form a complex in a predetermined ratio, and can be respectively isolated.

The composition of the present invention is stable under not only neutral conditions but also acidic conditions in the presence of protease, and it is also stable to heat. It has high affinity in a human body, and hence can exhibit a variety of activities of FGF in a human body.

The composition of the present invention can be prepared into formulations by optionally mixing it with a pharmaceutically acceptable additive, diluent, vehicle and analgesic agent as it is or according to any one of known pharmaceutical preparation methods, and these formulations may be administered parenterally or orally as a filled-in formulation, a suspension, a tablet, a capsule, granules, a powder and a solid-like or suspension-like formulation due to the above properties.

EXAMPLES

The present invention will be specifically described hereinafter by reference to Examples.

In addition, the bioactivity of bFGF used in the present invention was tested as follows. bFGF was diluted with a DMEM:F-12Ham medium in three stages, and these diluted solutions in an amount of 0.1 ml each were added to 96-well microplates (flat bottom). Then, 0.1 ml of a suspension of BHK-21 cells in a DMEM:F-12Ham medium ($3 \times 10^4$ cells/ml) was added in each plate. The cells were cultured for 3 days, and then fixed for 15 minutes by adding 40 µl of 5% glutaraldehyde. The plates were washed with methanol and PBS, and 200 µl of a BCA reagent was placed in the wells. The resultant mixtures were heated at 65° C. for 30 minutes and then measured for absorbance at 595 nm.

REFERENTIAL EXAMPLE 1

Synthesis of aluminum salt of β-cyclodextrin sulfate 10.0 Grams of β-cyclodextrin was dissolved in 500 ml of dimethylformamide (DMF), and 30 g of (CH$_3$)$_3$NSO$_3$ was added. The resultant mixture was stirred at 70° C. for 16 hours. The reaction mixture was cooled to room temperature, DMF was removed by decantation, and 1 liter of acetone was added. The precipitated crystal was recovered by filtration, and air-dried. 100 Milliliters of water was added to the air-dried crystal to form a solution, and then 150 ml of a 30% sodium acetate aqueous solution was added. The resultant mixture was stirred at room temperature for 4 hours, and 1.5 liters of ethanol was added. The mixture was allowed to stand overnight, and the precipitated crystal was recovered by filtration, dissolved in 150 ml of water, and dialyzed with a dialysis membrane at room temperature for 5 hours. The solution in the dialysis membrane was concentrated to about 150 ml at 50° C. under reduced pressure, and 1 liter of ethanol was added. The precipitated crystal was recovered by filtration, and dried at 60° C. under reduced pressure to give 20.5 g of a white powder. The white powder had a sulfur content of 14.95%.

Further, 10 g of the above crystal was dissolved in 250 ml of water, and 300 ml of a 2.8% aluminum chloride aqueous solution was added. Then, 2N sodium hydroxide was added to the resultant solution with stirring until the solution showed pH 4.5. The resultant mixture was stirred at room temperature for 1 hour, and the precipitate was centrifugally separated. The resultant crystal was dried under reduced pressure at 60° C. for 24 hours to give 10.0 g of a white powder. The thus-obtained aluminum salt of β-cyclodextrin sulfate had a sulfur content of 15.16%.

EXAMPLE 1

900 Microliters of distilled water was added to 25 mg of an aluminum salt of α-cyclodextrin sulfate, and the aluminum salt was fully suspended. Then, 100 μl of an aqueous solution containing 500 μg of bFGF was added to prepare a composition of bFGF and the aluminum salt of α-cyclodextrin sulfate.

A composition of bFGF and an aluminum salt of β-cyclodextrin sulfate, a composition of bFGF and an aluminum salt of γ-cyclodextrin sulfate and a composition of bFGF and an aluminum salt of 2-hydroxypropyl-β-cyclodextrin sulfate were prepared in the same manner as above.

EXAMPLE 2

900 Microliters of distilled water was added to 25 mg of an aluminum salt of β-cyclodextrin sulfate, and the aluminum salt was fully suspended. Then 100 μl of an aqueous solution containing 500 μg of bFGF was added to, and fully mixed with, the above-prepared suspension. The resultant mixture was freeze-dried to prepare a powdery composition of bFGF and the aluminum salt of β-cyclodextrin sulfate.

EXAMPLE 3

900 Microliters of distilled water was added to 25 mg of an aluminum salt of β-cyclodextrin sulfate, and the aluminum salt was fully suspended. Then 100 μl of an aqueous solution containing 500 μg of aFGF was added to, and fully mixed with, the above-prepared suspension. The resultant mixture was dried at 30° C. for 3 hours under reduced pressure to prepare a powdery composition of aFGF and the aluminum salt of β-cyclodextrin sulfate.

TEST EXAMPLE 1

A citric acid buffer solution having pH of 5.0 was added to each of the compositions obtained in the above Examples to extract bFGF, and each of the extracts was measured for bioactivity of bFGF. Table 1 shows the results.

As control, a bFGF aqueous solution containing no aluminum salt of cyclodextrin sulfate was used.

TABLE 1

| Composition | Bioactivity |
|---|---|
| Not treated | 100% |
| Composition of aluminum salt of α-cyclodextrin sulfate | 100% |
| Composition of aluminum salt of β-cyclodextrin sulfate | 100% |
| Composition of aluminum salt of γ-cyclodextrin sulfate | 100% |
| Composition of aluminum salt of 2-hydroxypropyl-β-cyclodextrin sulfate | 100% |

The compositions of stabilized bFGF showed 100% bFGF activity of non-treated bFGF, which shows that the bioactivity of bFGF was stably retained after bFGF formed complexes of the aluminum salts of cyclodextrin sulfates.

TEST EXAMPLE 2-1

Test on stability of bFGF in pepsin solution

Each of the compositions prepared in Example 1 was centrifugally separated, and 900 μl of the said supernatant was removed. 900 Microliters of a pH 1.2 disintegration test No. 1 solution in Japan Pharmacopoeia containing 50 μg of pepsin was added to each remainder, and the resultant mixtures were incubated at 37° C. for 6 hours. Then, the mixtures were measured for residual ratios of bFGF by an HPLC method. Table 2 shows the results.

As control, non-treated bFGF was used.

TABLE 2

| Composition | Residual ratio |
|---|---|
| Not treated | 0% |
| Composition of aluminum salt of α-cyclodextrin sulfate | 91% |
| Composition of aluminum salt of β-cyclodextrin sulfate | 96% |
| Composition of aluminum salt of γ-cyclodextrin sulfate | 85% |
| Composition of aluminum salt of 2-hydroxypropyl-β-cyclodextrin sulfate | 87% |

The non-treated bFGF showed a residual ratio of 0%, while bFGF in each of the compositions of aluminum salts of cyclodextrin sulfates was stably retained against decomposition by pepsin under severe conditions where the compositions were maintained in the presence of pepsin at 37° C for 6 hours.

TEST EXAMPLE 2-2

Test on stability of bFGF in pepsin solution

25 Milligrams of an aluminum salt of β-cyclodextrin sulfate was placed in a microtube, and 1 ml of an aqueous solution containing 250 μg of bFGF was added. The resultant mixture was vigorously mixed. The resultant suspension was centrifugally separated, and 900 μl of the supernatant was removed. 900 Microliters of a pH 1.2 disintegration test No. 1 solution in Japan Pharmacopoeia containing 50 μg of pepsin was added to the remainder, and the resultant mixture was incubated at 37° C. Then, the mixture was measured for a residual ratio of bFGF by an HPLC method.

Further, 25 mg of a sodium salt of β-cyclodextrin sulfate as a comparative substance was placed in a microtube, and 900 μl of a pH 1.2 disintegration test No. 1 solution in Japan Pharmacopoeia containing 50 μg of pepsin was added. Then, 100 μl of an aqueous solution containing 250 μg of bFGF was added, and the resultant mixture was incubated at 37° C. Then, the mixture was measured for a residual ratio of bFGF by an HPLC method. FIG. 1 shows the results.

As control, non-treated bFGF was used.

It has been found that the residual ratio of bFGF in the aluminum salt of β-cyclodextrin sulfate is stably maintained at a high level, while the residual ratio of bFGF in the sodium salt of β-cyclodextrin sulfate sharply decreases.

TEST EXAMPLE 3-1

Test on stability of bFGF in chymotrypsin solution

Each of the compositions prepared in Example 1 was centrifugally separated, and 900 μl of the supernatant each was removed. Then, 900 μl of a 20 mM phosphoric acid buffer solution having pH of 7.4 and containing 50 μg of chimotrypsin was added, and each of the resultant mixtures was incubated at 37° C. for 24 hours. Then, the mixtures were measured for residual ratios of bFGF by an HPLC method. Table 3 shows the results.

TABLE 3

| Composition | Residual ratio |
| --- | --- |
| Not treated | 0% |
| Composition of aluminum salt of α-cyclodextrin sulfate | 81% |
| Composition of aluminum salt of β-cyclodextrin sulfate | 78% |
| Composition of aluminum salt of γ-cyclodextrin sulfate | 93% |
| Composition of aluminum salt of 2-hydroxypropyl-β-cyclodextrin sulfate | 82% |

The non-treated bFGF showed a residual ratio of 0%, while bFGF in each of the compositions of aluminum salts of cyclodextrin sulfates was stably retained against such protease as chimotrypsin under severe conditions where the compositions were maintained in the presence of chimotrypsin at 37° C. for 24 hours.

TEST EXAMPLE 3-2

Test on stability of bFGF in chymotrypsin solution

Figure 2:
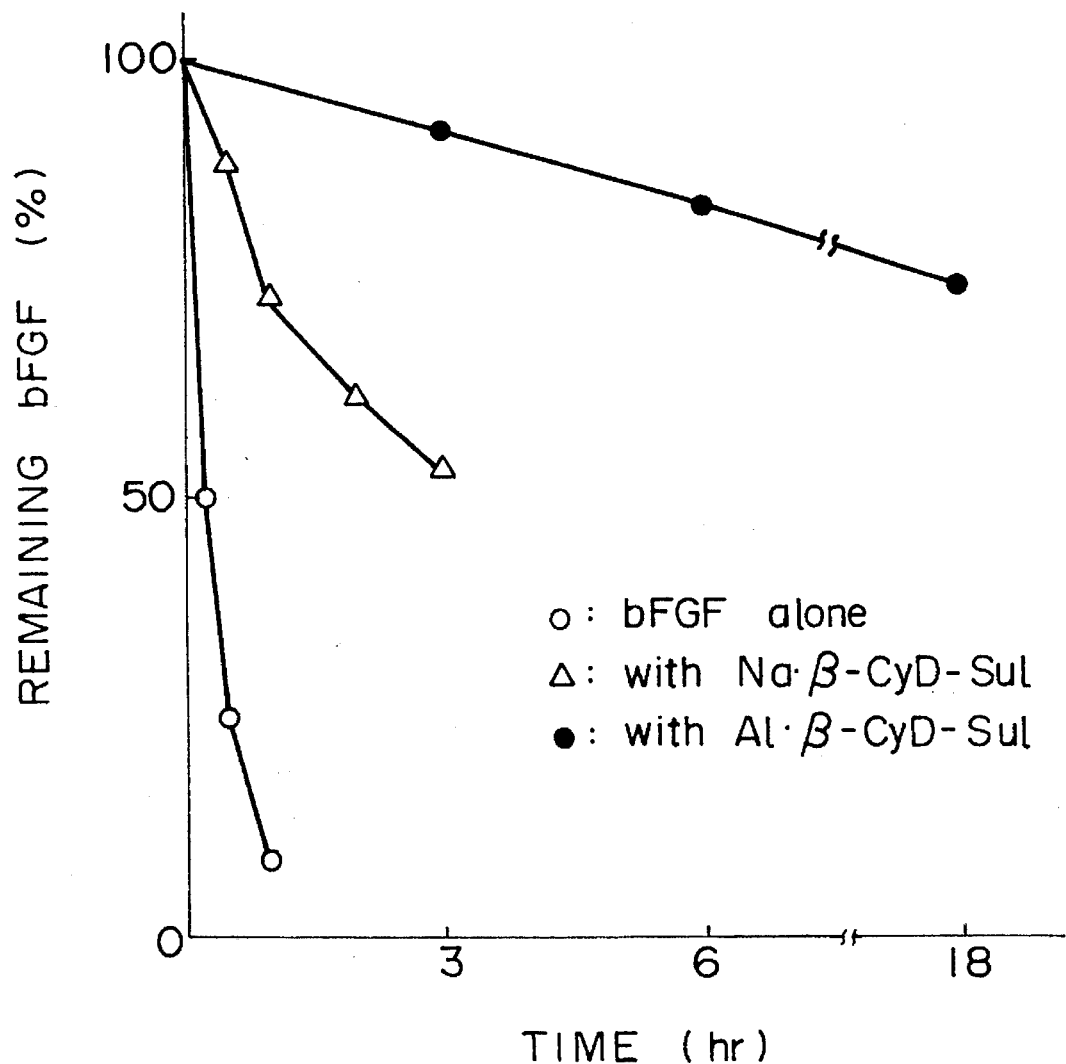

Test Example 2-2 was repeated except that each of 900 μl of the pH 1.2 disintegration test No. 1 solutions in Japan Pharmacopoeia containing 50 μg of pepsin was replaced with 900 μl of a 20 mM phosphoric acid buffer solution having pH of 7.4 and containing 50 μg of chimotrypsin. Then, the resultant mixtures were incubated at 37° C., and measured for residual ratios of bFGF by an HPLC method. FIG. 2 shows the results.

As control, non-treated bFGF was used.

It has been found that the residual ratio of bFGF in the aluminum salt of β-cyclodextrin sulfate is stably maintained at a high level, while the residual ratio of bFGF in the sodium salt of β-cyclodextrin sulfate sharply decreases.

The above test results suggest the following. bFGF adsorbed on an aluminum salt of β-cyclodextrin sulfate is more remarkably stably retained against proteases such as pepsin which shows its activity under acidic conditions and chimotrypsin which shows its activity under nearly neutral conditions than bFGF adsorbed on a sodium salt of β-cyclodextrin sulfate. Therefore, when bFGF is orally administered as an anti-peptic-ulcer formulation, bFGF stabilized by an aluminum salt of β-cyclodextrin sulfate is very useful.

TEST EXAMPLE 4

Test on therapy of gastric ulcer

Male rats (Jcl: Wistar) aged 7 weeks were used. Laparotomy by epigastric incision was made in each rat under ether anesthesia, and while a pipe having a diameter of 6 mm was applied to a site in the boundary between the stomach body portion and the pyloric portion from the serous membrane side, 50 μl of acetic acid was injected over 20 seconds. Then, the acetic acid was removed, and the serous membrane was washed with a saline solution and closed.

The above rats were orally administered with a drug once a day for 10 days from one day after the operative day. The rats were sacrificed with ether one day after the last administration, and the areas ($mm^2$) of the ulcers were measured. Table 4 shows the results.

Control: water bFGF: 10 μg/kg

Composition of aluminum salt of α-cyclodextrin sulfate: bFGF 10 μg/kg

Cimetidine: 200 mg/kg

TABLE 4

| Drug | Dose | Number of rats | Ulcer index | Improvement ratio |
| --- | --- | --- | --- | --- |
| Control | | 10 | 6.5 ± 2.3 | |
| bFGF | 10 μg bFGF/kg | 10 | 5.5 ± 2.0 | 15% |
| Composition of aluminum salt of α-cyclodextrin sulfate | 10 μg bFGF/kg | 10 | 2.5 ± 1.0* | 62% |
| Cimetidine | 200 mg/kg | 10 | 4.5 ± 1.7 | 31% |

*$P<0.01$ vs. Control (Dunnett)

It has been found that the administration of the composition of the present invention has a healing effect of bFGF on gastric ulcer.

TEST EXAMPLE 5

Granulation tissue formation test:
Preparation of samples:

There was prepared a solution containing 500 μg/ml of bFGF from water for injection. And, 500 μl of the solution was added to 25 mg of an aluminum salt of β-cyclodextrin sulfate, 25 mg of a sodium salt of β-cyclodextrin sulfate and 25 mg of an aluminum hydroxide, respectively, to prepare three samples. Each vehicle in the absence of bFGF was used as control. The sample containing an aluminum salt of β-cyclodextrin sulfate and the sample containing aluminum hydroxide were fully suspended before use.

Male rats (Wistar) aged 7 weeks were used. 20 μl of each sample was injected in the center of paper disk (diameter 8 mm, thickness 1 mm, supplied by Toyo Filter Paper K. K.), and the paper disks were implanted subcutaneously into left and right sites of mid-dorsal line in the skin. Seven days after implantation, the rats were sacrificed under ether anesthesia, and the paper disks and granulation tissue surrounding them were carefully removed and weighed. The weights of the paper disks and the aluminum salf of β-cyclodextrin sulfate or the aluminum hydroxide were corrected to determine wet weights (mg) of the granulation tissue. Table 5 shows the results.

TABLE 5

| Composition | Wet Weight (mg) | | | |
|---|---|---|---|---|
| | Water | Aluminum hydroxide | Sodium salt of β-cyclodextrin sulfate | Aluminum salt of β-cyclodextrin sulfate |
| Control | 98.3 ± 2.2 | 128.4 ± 3.7 | 91.5 ± 6.0 | 102.3 ± 1.8 |
| bFGF | 350 ± 46.3 | 234 ± 17.4 | 283 ± 19.1 | 1,139 ± 167.4 |

The number of the rats per each test group was four.

bFGF promotes granulation tissue with the proliferation of fibroblast and vascularization in the wound healing. Therefore, bFGF was tested on the effect on the granulation tissue formation while it was adsorbed. As a result, all samples containing bFGF exhibited a significant increase in the wet weights of the paper disks as compared with that of each vehicle. Further, the composition of bFGF and an aluminum salt of β-cyclodextrin sulfate showed a significant increase in the wet weight of the paper disk as compared with the aqueous solution containing bFGF, the composition of bFGF and a sodium salt of β-cyclodextrin sulfate, and the composition containing bFGF and aluminum hydroxide.

According to the present invention, FGF can be stabilized by forming a complex of FGF with an aluminum salt of cyclodextrin sulfate, and can be prepared into formulations in a stable state.

What is claimed is:

1. A composition of a stabilized fibroblast growth factor, which contains a complex wherein a fibroblast growth factor is adsorbed on the aluminum salt of cyclodextrin sulfate composed of a member selected from the group consisting of an aluminum salt of β-cyclodextrin, an aluminum salt of β-cyclodextrin, an aluminum salt of β-cyclodextrin, an aluminum salt of hydroxypropyl-α-cyclodextrin, an aluminum salt of hydroxypropyl-β-cyclodextrin, an aluminum salt of hydroxypropyl-γ-cyclodextrin, an aluminum salt of hydroxyethyl-α-cyclodextrin, an aluminum salt of hydroxyethyl-β-cyclodextrin, an aluminum salt of hydroxyethyl-γ-cyclodextrin; and wherein the number of aluminum ions per cyclodextrin sulfate is at least two.

2. A composition according to claim 1, wherein the fibroblast growth factor is a basic fibroblast growth factor.

3. A composition according to claim 2, wherein the fibroblast growth factor is a human basic fibroblast growth factor.

4. A composition according to claim 1 of a stabilized fibroblast growth factor, wherein a fibroblast growth factor is adsorbed on an aluminum salt of cyclodextrin sulfate.

5. A composition according to claim 1, which is in the form of a powder.

6. A composition according to claim 1, wherein the fibroblast growth factor and the aluminum salt of cyclodextrin sulfate are contained in a weight ration of 1:2 to 1:500.

7. A method of stabilizing a fibroblast growth factor, which comprises admixing a fibroblast growth factor with an aluminum salt of cyclodextrin sulfate of claim 1.

8. A composition according to claim 1, wherein the number of aluminum ions per cyclodextrin sulfate is at least four.

* * * * *